United States Patent
Ji (10) Patent No.: US 11,396,232 B2
(45) Date of Patent: Jul. 26, 2022

(54) VEHICLE CONTROL DEVICE, VEHICLE CONTROL METHOD AND HEAD-UP DISPLAY APPARATUS

(71) Applicant: BOE TECHNOLOGY GROUP CO., LTD., Beijing (CN)

(72) Inventor: Chunyan Ji, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 418 days.

(21) Appl. No.: 16/106,413

(22) Filed: Aug. 21, 2018

(65) Prior Publication Data

US 2019/0061525 A1    Feb. 28, 2019

(30) Foreign Application Priority Data

Aug. 22, 2017   (CN) .......................... 201710723986.9

(51) Int. Cl.
| | | |
|---|---|---|
| *B60K 28/06* | (2006.01) | |
| *A61B 5/18* | (2006.01) | |
| *G02B 27/01* | (2006.01) | |
| *G02B 27/00* | (2006.01) | |
| *A61B 5/00* | (2006.01) | |
| *A61B 5/374* | (2021.01) | |
| *A61B 5/375* | (2021.01) | |

(52) U.S. Cl.
CPC ................ *B60K 28/06* (2013.01); *A61B 5/18* (2013.01); *A61B 5/374* (2021.01); *A61B 5/375* (2021.01); *A61B 5/742* (2013.01); *G02B 27/0018* (2013.01); *G02B 27/0101* (2013.01)

(58) Field of Classification Search
CPC .............................. B60K 28/06; A61B 5/0476
See application file for complete search history.

(56) References Cited

U.S. PATENT DOCUMENTS

| | | | |
|---|---|---|---|
| 2008/0167569 A1* | 7/2008 | Ermes ..................... | A61B 5/369 600/544 |
| 2010/0156617 A1* | 6/2010 | Nakada .................. | A61B 3/113 340/439 |
| 2016/0001781 A1* | 1/2016 | Fung ...................... | B60K 28/02 701/36 |
| 2018/0186234 A1* | 7/2018 | Mestha .................. | H04N 7/181 |

FOREIGN PATENT DOCUMENTS

| | | |
|---|---|---|
| CN | 102047304 A | 5/2011 |
| CN | 203226817 U | 10/2013 |
| CN | 103505224 A | 1/2014 |

(Continued)

OTHER PUBLICATIONS

First Office Action for Chinese Application No. 201710723986.9, dated Mar. 4, 2019, 7 Pages.

*Primary Examiner* — Imran K Mustafa (74) *Attorney, Agent, or Firm* — Brooks Kushman P.C.

(57) ABSTRACT

The present disclosure provides a vehicle control device, a vehicle control method and a head-up display apparatus. The vehicle control device includes: an extraction circuit used to extract brain wave signals of a user; and a control circuit used to determine whether the user is in an unsafe driving state according to the brain wave signals, and perform at least one of operations including issuing a warning reminder and controlling vehicle deceleration when determining that the user is in the unsafe driving state.

6 Claims, 4 Drawing Sheets

(56) References Cited

FOREIGN PATENT DOCUMENTS

| | | |
|---|---|---|
| CN | 104724089 A | 6/2015 |
| CN | 106529421 A | 3/2017 |
| CN | 206179162 U | 5/2017 |
| CN | 106859644 A | 6/2017 |
| CN | 107015632 A | 8/2017 |
| KR | 101447060 B1 | 10/2014 |

\* cited by examiner

United States Patent

VEHICLE CONTROL DEVICE, VEHICLE CONTROL METHOD AND HEAD-UP DISPLAY APPARATUS

CROSS-REFERENCE TO RELATED APPLICATION

This application claims priority to Chinese Patent Application No. 201710723986.9, filed on Aug. 22, 2017, which is incorporated herein by reference in its entirety.

TECHNICAL FIELD

The present disclosure relates to the field of head up display device, and in particular to a vehicle control device, a vehicle control method and a head-up display apparatus.

BACKGROUND

Driving requires a high degree of concentration, and users' behaviors such as fatigue driving, drunk driving and driving calls are important factors causing frequent vehicle accidents. Vehicle mounted head-up display apparatus have become research hotspots in recent years because they can free drivers' hands and improve safety of driving. In control systems based on the vehicle mounted head-up display apparatus, gesture and voice are the most frequently used interaction modes. However, gesture recognition requires one hand to leave the steering wheel, and this distracts the users' attention and then increases the risk of driving safety. Although voice control is safer, it requires the users to remember a lot of voice commands and has poor recognition accuracy, and it is often disturbed by noise and easy to make the users feel anxious; moreover, it also limits demands of some special groups.

Currently, there are still many problems with the head-up display apparatus, such as insufficient brightness of images, affecting observation of road conditions, forming a reflective halo on a windshield and picture ghosting.

SUMMARY

According to a first aspect, the present disclosure provides a vehicle control device, which includes an extraction circuit configured to extract brain wave signals of a user and a control circuit configured to determine whether the user is in an unsafe driving state according to the brain wave signals, and perform at least one of operations including issuing a warning reminder and controlling vehicle deceleration when determining that the user is in the unsafe driving state.

In some embodiment of the present disclosure, the control circuit is further configured to, according to the brain wave signals, determine whether a proportion of $\theta$ waves in the brain wave signals exceeds a $\theta$ wave threshold, whether a proportion of $\beta$ waves in the brain wave signals exceeds a $\beta$ wave threshold, or whether a proportion of $\gamma$ waves in the brain wave signals exceeds a $\gamma$ wave threshold. When determining that the proportion of $\theta$ waves in the brain wave signals exceeds the $\theta$ wave threshold, the proportion of $\beta$ waves in the brain wave signals exceeds the $\beta$ wave threshold, or the proportion of $\gamma$ waves in the brain wave signals exceeds the $\gamma$ wave threshold, the control circuit performs at least one of operations including issuing the warning reminder and controlling vehicle deceleration.

In some embodiment of the present disclosure, the $\theta$ wave has a frequency of 4 Hz-7 Hz as well as an amplitude of 5 $\mu V$-20 $\mu V$; the $\beta$ wave has a frequency of 14 Hz-30 Hz as well as an amplitude of 100 $\mu V$-150 $\mu V$; and the $\gamma$ wave has a frequency of 30 Hz-80 Hz.

In some embodiment of the present disclosure, the control circuit is further configured to calculate a time period during which the user is in the unsafe driving state; when the time period during which the user is in the unsafe driving state exceeds an unsafe time threshold, the control circuit controls a vehicle to stop.

In some embodiment of the present disclosure, the vehicle control device further includes: a push circuit configured to push an operation instruction for the user. The control circuit is further configured to determine whether the user is concerned about the operation instruction according to the brain wave signals of the user; when determining that the user is concerned about the operation instruction, the control circuit issues an instruction for performing corresponding operation.

In some embodiment of the present disclosure, the control circuit is further configured to, after the push circuit pushes the operation instruction for the user, determine whether a proportion of $\alpha$ waves in the brain wave signals of the user exceeds a $\alpha$ wave threshold according to the brain wave signals of the user; and determine that the user is concerned about the operation instruction, when the proportion of $\alpha$ waves in the brain wave signals of the user exceeds the $\alpha$ wave threshold.

In some embodiment of the present disclosure, the operation instruction includes at least one of a vehicle turning instruction, a speed instruction, a call connection instruction, a backlight brightness adjustment instruction or a music play instruction.

In some embodiment of the present disclosure, the $\theta$ wave has a frequency of 4 Hz-7 Hz as well as an amplitude of 5 $\mu V$-20 $\mu V$.

In some embodiment of the present disclosure, the extraction circuit includes an electrode cap.

According to a second aspect, the present disclosure provides a vehicle control method, which includes: extracting brain wave signals of a user; determining whether the user is in an unsafe driving state according to the brain wave signals; and performing at least one of operations including issuing a warning reminder and controlling vehicle deceleration when determining that the user is in the unsafe driving state.

In some embodiment of the present disclosure, the determining whether the user is in an unsafe driving state according to the brain wave signals includes: determining whether a proportion of $\theta$ waves in the brain wave signals exceeds a $\theta$ wave threshold, and whether a proportion of $\beta$ waves in the brain wave signals exceeds a $\beta$ wave threshold, or whether a proportion of $\gamma$ waves in the brain wave signals exceeds a $\gamma$ wave threshold.

In some embodiment of the present disclosure, the $\theta$ wave has a frequency of 4 Hz-7 Hz as well as an amplitude of 5 $\mu V$-20 $\mu V$; the $\beta$ wave has a frequency of 14 Hz-30 Hz as well as an amplitude of 100 $\mu V$-150 $\mu V$; and the $\gamma$ wave has a frequency of 30 Hz-80 Hz.

In some embodiment of the present disclosure, the vehicle control method further includes: calculating a time period during which the user is in the unsafe driving state; when the time period during which the user is in the unsafe driving state exceeds an unsafe time threshold, controlling a vehicle to stop.

In some embodiment of the present disclosure, the vehicle control method further includes: pushing an operation instruction for the user; determining whether the user keeps concern about the operation instruction according to the brain wave signals of the user; and issuing an instruction for performing corresponding operation, when determining that the user keeps concern about the operation instruction. The operation instruction includes at least one of a vehicle turning instruction, a speed instruction, a call connection instruction, a backlight brightness adjustment instruction or a music play instruction.

In some embodiment of the present disclosure, the determining whether the user keeps concern about the operation instruction according to the brain wave signals of the user includes: after pushing the operation instruction for the user, determining whether a proportion of α waves in the brain wave signals of the user exceeds a α wave threshold according to the brain wave signals of the user; and when determining that the proportion of α waves in the brain wave signals of the user exceeds the α wave threshold, determining that the user keeps concern about the operation instruction.

According to a third aspect, the present disclosure provides a head-up display apparatus, which includes an obtaining device, a display device, a projection device, a display medium and the above vehicle control device. An image displayed on the display device is projected onto the display medium through the projection device. The obtaining device is configured to obtain position information of a gaze point of the user's eyes on the display medium or the display device. The control circuit of the vehicle control device is configured to issues an instruction for performing an operation corresponding to the position information according to the position information of the gaze point.

In some embodiment of the present disclosure, the obtaining device includes: an infrared emitter configured to emit infrared light towards eyes of the user, thereby forming light reflection points in the two pupils of eyes of the user; and a position calculation circuit configured to determine the position information of a gaze point of the user's eyes on the display medium or the display device according to the reflection points.

In some embodiment of the present disclosure, a wedge-shaped transflective film is disposed at an inner surface of the display medium; and the transflective film has a thickness that is gradually increased from a bottom of the vehicle to a top of the vehicle.

In some embodiment of the present disclosure, the display medium is a front windshield of the vehicle; and an angle defined between an inner surface of the transflective film and an outer surface of the transflective film is in a range of from 0.02-2.2 degrees.

In some embodiment of the present disclosure, the head-up display apparatus further includes: an ambient light detection device configured to detect brightness of ambient light. The control circuit is configured to, when the brightness of the ambient light is less than a first brightness threshold and the gaze point is not at the display medium and the display device, send an instruction for reducing backlight brightness to the display device. The control circuit is further configured to, when the brightness of the ambient light is greater than a second brightness threshold and the gaze point is at the display medium and the display device, send an instruction for increasing backlight brightness to the display device.

BRIEF DESCRIPTION OF THE DRAWINGS

A brief introduction will be given hereinafter to the accompanying drawings which will be used in the description of the embodiments in order to explain the embodiments of the present disclosure more clearly. Apparently, the drawings in the description below are merely for illustrating some embodiments of the present disclosure. Those skilled in the art may obtain other drawings according to these drawings without paying any creative labor.

DETAILED DESCRIPTION

Reference will now be made in detail to exemplary embodiments, examples of which are illustrated in the accompanying drawings. The following description refers to the accompanying drawings in which the same numbers in different drawings represent the same or similar elements unless otherwise indicated. The following description of exemplary embodiments is merely used to illustrate the present disclosure and is not to be construed as limiting the present disclosure.

Unless otherwise defined, any technical or scientific terms used herein shall have the common meaning understood by a person of ordinary skills. Such words as "first" and "second" used in the specification and claims are merely used to differentiate different components rather than to represent any order, number or importance. Similarly, such words as "one" or "one of" are merely used to represent the existence of at least one member, rather than to limit the number thereof. Such words as "connect" or "connected to" may include electrical connection, direct or indirect, rather than being limited to physical or mechanical connection. Such words as "on/above", "under/below", "left" and "right" are merely used to represent relative position relationship, and when an absolute position of an object is changed, the relative position relationship will be changed too.

With development of human-machine interaction technology, the Human-machine interaction technology has gradually changed towards intelligent interaction and natural interaction. The focus of human-machine interaction has also developed from defining interaction modes and designing interaction semantics to focusing on users' brain waves, and then mining the users' implicit needs. The brain waves are formed after synaptic potentials of a large number of neurons simultaneously occur when the brain is active. The brain waves record changes of radio waves of the brain when the brain is active, and are overall reflection of the electrophysiological activity of the brain's nerve cells on the surface of the cerebral cortex or scalp. Thus, the brain waves are important biological signals and characterize activity of the human brains.

Figure 1:
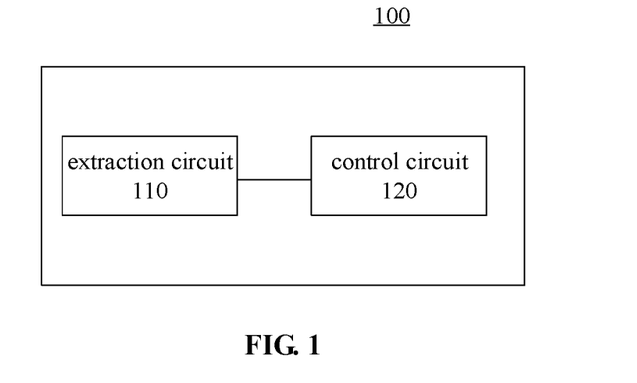
FIG. 1 is a schematic block diagram of a vehicle control device according to an embodiment of the present disclosure.

FIG. 1 is a schematic block diagram of a vehicle control device according to an embodiment of the present disclosure. As shown in FIG. 1, in one embodiment of the present disclosure, a vehicle control device 100 includes an extraction circuit 110 and a control circuit 120. In one embodiment, the extraction circuit 110 is used to extract brain wave signals of a user. The control circuit 120 is used to determine whether the user is in an unsafe driving state according to the brain wave signals. If it is determined that the user is in an unsafe driving state, the control circuit 120 is used to issue a warning reminder and/or control vehicle deceleration. As can be seen, the vehicle control device of one embodiment of the present disclosure may determine whether the user is in the unsafe driving state according to the brain wave signals, and makes corresponding reminders or deceleration controls. In this way, the safety of user driving and the recognition accuracy are improved.

Optionally, the warning reminder may include a text reminder and/or a voice reminder, to remind the user to be in the unsafe driving state at this time. Accordingly, the user may take corresponding operations such as vehicle deceleration operation, and parking operation. Optionally, contents of the warning reminder are small and concise, so that the user can timely notice the warning reminder. It should be noted that, the brain wave signals of the user may be collected by an electroencephalogram detection device such as a headset device. Specifically, the electroencephalogram detection device may be an electrode cap. The electroencephalogram detection device may be coupled to the vehicle control device 100 by means of Bluetooth, wired communication or wireless communication, so as to transfer collected brain wave signals to the vehicle control device 100.

By using the extraction circuit 110 and the control circuit 120 to determine whether the user is in the unsafe driving state according to the brain wave signals, the vehicle control device 100 makes corresponding controls, thereby ensuring the safety of the user (driver). The accuracy of an electroencephalogram vehicle control is higher than that of other vehicle control modes, and the electroencephalogram recognition is difficult to replicate and unique, and this reduces driving safety risk and improves the recognition accuracy.

The brain waves are spontaneous rhythmic neuroelectrical activities, and classification of waveforms of the brain waves is mainly based on frequencies of the brain waves. Generally, a waveform with a slow frequency has large amplitude, and a waveform with high frequency has small amplitude. The brain waves with a frequency range of 1-30 times per second can be divided into four bands: $\delta$ wave with a frequency of 1 Hz-3 Hz as well as an amplitude of 20 $\mu V$-200 $\mu V$; $\theta$ wave with a frequency of 4 Hz-7 Hz as well as an amplitude of 5 $\mu V$-20 $\mu V$; $\alpha$ wave with a frequency of 8 Hz-13 Hz (with an average of 10 Hz) as well as an amplitude of 20 $\mu V$-100 $\mu V$; $\beta$ wave with a frequency of 14 Hz-30 Hz as well as an amplitude of 100 $\mu V$-150 $\mu V$. In addition, when awakening and concentrating on something, $\gamma$ wave with a higher frequency than the beta wave is found. The $\gamma$ wave has a frequency of 30 Hz-80 Hz, and has an uncertain amplitude range. During sleep, other normal brain waves with more special waveforms may appear, such as hump wave, $\sigma$ wave, $\lambda$ wave, $\kappa$-composite wave. Generally speaking, in a state of tension, the brain produces $\beta$ waves; when the body relaxes, the brain is active and the inspiration is constant, the brain produces $\alpha$ waves; when feeling sleepy, the brain produces $\theta$ waves; when entering deep sleep, the brain produces $\delta$ waves.

As one embodiment of the present disclosure, the control circuit 120 is used to, according to the brain wave signals, determine whether a proportion of $\theta$ waves in the brain wave signals exceeds a $\theta$ wave threshold, and whether a proportion of $\beta$ waves in the brain wave signals exceeds a $\beta$ wave threshold, or whether a proportion of $\gamma$ waves in the brain wave signals exceeds a $\gamma$ wave threshold. When a judgment result is yes, then the control circuit 120 issues a warning reminder and/or control vehicle deceleration. It should be noted, when the proportion of $\theta$ waves in the brain wave signals exceeds the $\theta$ wave threshold, and the proportion of $\beta$ waves in the brain wave signals exceeds the $\beta$ wave threshold, or the proportion of $\gamma$ waves in the brain wave signals exceeds the $\gamma$ wave threshold, it is determined that the user is in an unsafe driving state. The unsafe driving state may include at least one of fatigue, distraction, or excitement. The $\theta$ wave threshold, $\beta$ wave threshold and $\gamma$ wave threshold may be set in advance. Optionally, different $\theta$ wave thresholds, $\beta$ wave thresholds and $\gamma$ wave thresholds may be preset for different users, to meet individual differences between the users. In one embodiment, the vehicle control device 100 may determine a psychological state, an emotional state and a concentration of the user based on parameters such as frequency intensity, amplitude and proportion of the brain wave signals. Once detecting that the user is in the unsafe driving state, the vehicle control device 100 immediately issues a warning reminder and/or controls vehicle deceleration.

As another embodiment of the present disclosure, the extraction circuit 110 is used to pre-process the brain wave signals of the user. The brain wave signals of the user is pre-processed and then waveforms of the pre-processed brain waves are taken as a judgment object, thereby improving regularization of waveforms of the brain waves and improving the working efficiency of the control circuit 120. Optionally, the pre-processing may include, but not limited to, amplification, conversion, denoising, or analysis, thereby obtaining brainwave signals that are convenient for subsequent information processing.

As another embodiment of the present disclosure, the control circuit 120 is further used to calculate a time period during which the user is in the unsafe driving state. When the time period exceeds an unsafe time threshold, the control circuit 120 controls a vehicle to stop. Specifically, when the control circuit 120 determines that the user is in the unsafe driving state, the control circuit 120 issues a warning reminder and/or controls vehicle deceleration; meanwhile, the control circuit 120 starts timing and calculates the time period during which the user is in the unsafe driving state. When the time period during which the user is in the unsafe driving state exceeds the unsafe time threshold, the control circuit 120 controls the vehicle to stop. Optionally, the time period during which the user is in the unsafe driving state means a time period during which the user is continuously in the unsafe driving state. Thus, when continuously detecting that the user's unsafe driving state exceeds a certain time limit, the vehicle control device can control the vehicle to stop, thereby ensure the user's safe driving.

Figure 2:
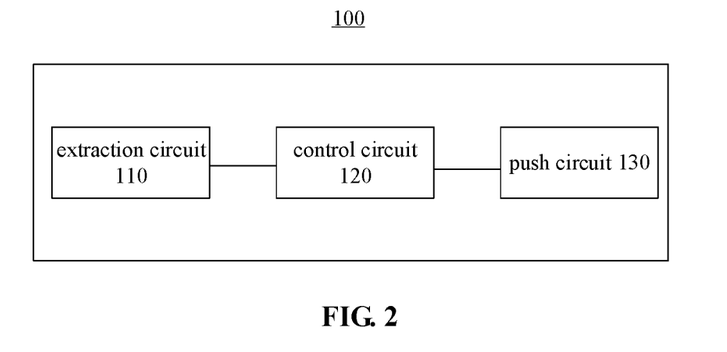
FIG. 2 is a schematic block diagram of a vehicle control device according to another embodiment of the present disclosure.

As another embodiment of the present disclosure, as shown in FIG. 2, on the basis of FIG. 1, in addition to the extraction circuit 110 and the control circuit 120, the vehicle control device further includes a push circuit 130. The push circuit 130 is used to push an operation instruction for the user. The push circuit 130 is further used to determine whether the user is concerned about the operation instruction according to the brain wave signals of the user. When it is determined that the user is concerned about the operation instruction, the push circuit 130 issues an instruction for performing corresponding operation. Specifically, after the push circuit 130 pushes one operation instruction for the user; the push circuit 130 determines whether a proportion of α waves in the brain wave signals of the user exceeds a α wave threshold according to the brain wave signals of the user; the push circuit 130 issues an instruction for performing corresponding operation when determining that the proportion of α waves in the brain wave signals of the user exceeds the α wave threshold. Optionally, the push circuit 130 is used to push the operation instruction for the user according to the user's behavior habits. The operation instruction may include a vehicle turning instruction, a speed instruction, a call connection instruction, a backlight brightness adjustment instruction, a music play instruction, and so on. In one embodiment, the push circuit 130 may be implemented as a processor.

Thus, when the user needs to manipulate an instruction, the user only needs to keep a high degree of concern about the pushed operation instruction to enable the proportion of α waves in the brain wave signals of the user to exceed the α wave threshold, then the push circuit 130 issues an instruction for performing corresponding operation so as to control corresponding components to perform corresponding operation. Therefore, under help of the above vehicle control device 100, the user's sight does not need to leave front road all the time, and the user only needs to control his brain waves, thereby greatly improving security.

As another embodiment of the present disclosure, the push circuit 130 is used to calculate a time period during which the user keeps concern about the operation instruction according to the brain wave signals of the user. When the time period during which the user keeps concern about the operation instruction exceeds a concern time threshold, the push circuit 130 issues an instruction for performing corresponding operation. Specifically, the push circuit 130 determines whether the proportion of α waves in the brain wave signals of the user exceeds the α wave threshold according to the brain wave signals of the user; when determining that the proportion of α waves in the brain wave signals of the user exceeds the α wave threshold, the push circuit 130 starts timing; when the time period during which the user keeps concern about the operation instruction exceeds the concern time threshold, the push circuit 130 issues an instruction for performing corresponding operation.

Based on the same idea, one embodiment of the present disclosure further provides a vehicle control method which can solve the same technical problem and achieves the same technical effects.

Figure 3:
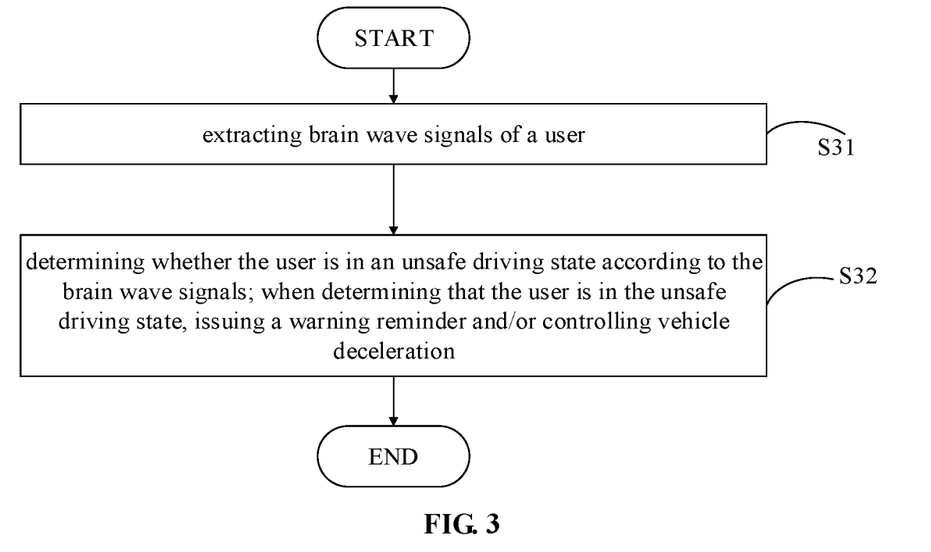
FIG. 3 is a flow chart of a vehicle control method according to an embodiment of the present disclosure.

As one embodiment of the present disclosure, as shown in FIG. 3, the vehicle control method includes: step S31 of extracting brain wave signals of a user; and step S32 of determining whether the user is in an unsafe driving state according to the brain wave signals; when determining that the user is in the unsafe driving state, issuing a warning reminder and/or controlling vehicle deceleration.

As can be seen, the vehicle control method of one embodiment of the present disclosure may determine whether the user is in the unsafe driving state according to the brain wave signals, and makes corresponding reminders or deceleration controls when the user is in the unsafe driving state. In this way, the safety of user driving and the recognition accuracy are improved.

Optionally, the warning reminder may include a text reminder and/or a voice reminder, to remind the user to be in the unsafe driving state at this time. Accordingly, the user may take corresponding operations such as vehicle deceleration operation, and parking operation. Optionally, contents of the warning reminder are small and concise, so that the user can timely notice the warning reminder. It should be noted that, the brain wave signals of the user may be collected by an electroencephalogram detection device such as a headset device. Specifically, the electroencephalogram detection device may be an electrode cap.

By determining whether the user is in the unsafe driving state according to the brain wave signals, the vehicle control method makes corresponding controls, thereby ensuring the safety of the user (driver). The accuracy of an electroencephalogram vehicle control is higher than that of other vehicle control modes, and the electroencephalogram recognition is difficult to replicate and unique, and this reduces driving safety risk and improves the recognition accuracy.

The determining whether the user is in an unsafe driving state according to the brain wave signals includes: determining whether a proportion of θ waves in the brain wave signals exceeds a θ wave threshold, and whether a proportion of β waves in the brain wave signals exceeds a β wave threshold, or whether a proportion of γ waves in the brain wave signals exceeds a γ wave threshold; when a judgment result is yes, then issuing a warning reminder and/or controlling vehicle deceleration. It should be noted, when the proportion of θ waves in the brain wave signals exceeds the θ wave threshold, the proportion of β waves in the brain wave signals exceeds the β wave threshold, or the proportion of γ waves in the brain wave signals exceeds the γ wave threshold, it is determined that the user is in the unsafe driving state. The unsafe driving state may include at least one of fatigue, distraction, or excitement. The θ wave threshold, β wave threshold and γ wave threshold may be set in advance. Optionally, different θ wave thresholds, β wave thresholds and γ wave thresholds may be preset for different users, to meet individual differences between the users. In one embodiment, the vehicle control device 100 may determine a psychological state, an emotional state and a concentration of the user based on parameters such as frequency intensity, amplitude and proportion of the brain wave signals. Once detecting that the user is in the unsafe driving state, the vehicle control method immediately issues a warning reminder and/or controls vehicle deceleration.

As another embodiment of the present disclosure, the extracting brain wave signals of a user includes: pre-processing the brain wave signals of the user. The brain wave signals of the user are pre-processed and then waveforms of the pre-processed brain waves are taken as a judgment object, thereby improving regularization of waveforms of the brain waves. Optionally, the pre-processing may include, but not limited to, amplification, conversion, denoising, or analysis, thereby obtaining brainwave signals that are convenient for subsequent information processing.

As another embodiment of the present disclosure, the vehicle control method further includes calculating a time period during which the user is in the unsafe driving state; when the time period exceeds an unsafe time threshold, controlling a vehicle to stop.

Figure 4:
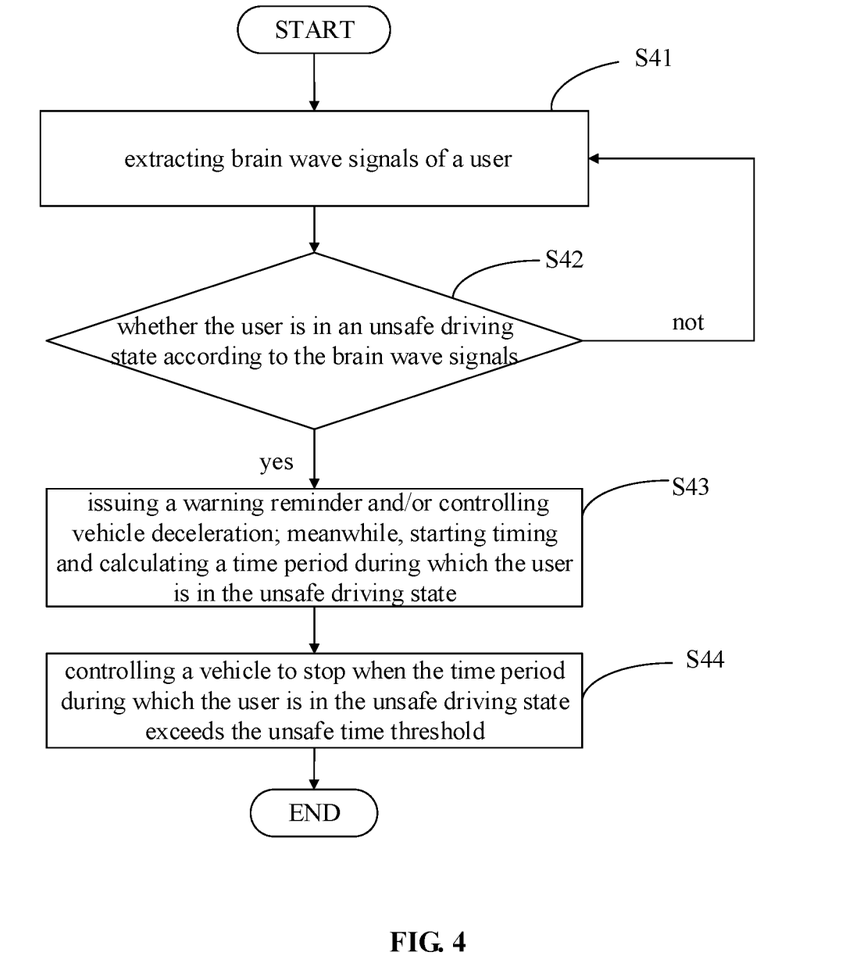
FIG. 4 is a flow chart of a vehicle control method according to another embodiment of the present disclosure.

Specifically, FIG. 4 is a flow chart of a vehicle control method according to another embodiment of the present disclosure. As shown in FIG. 4, the vehicle control method includes: step S41 of extracting brain wave signals of a user; step S42 of determining whether the user is in an unsafe driving state according to the brain wave signals; when determining that the user is in the unsafe driving state, performing the step S43; otherwise, performing the step S41; step S43 of issuing a warning reminder and/or controlling vehicle deceleration; meanwhile, starting timing and calculating a time period during which the user is in the unsafe driving state; and step S44 of controlling a vehicle to stop when the time period during which the user is in the unsafe driving state exceeds the unsafe time threshold.

Optionally, the time period during which the user is in the unsafe driving state means a time period during which the user is continuously in the unsafe driving state. Thus, when continuously detecting that the user's unsafe driving state exceeds a certain time limit, the vehicle control device can control the vehicle to stop, thereby ensure the user's safe driving.

Figure 5:
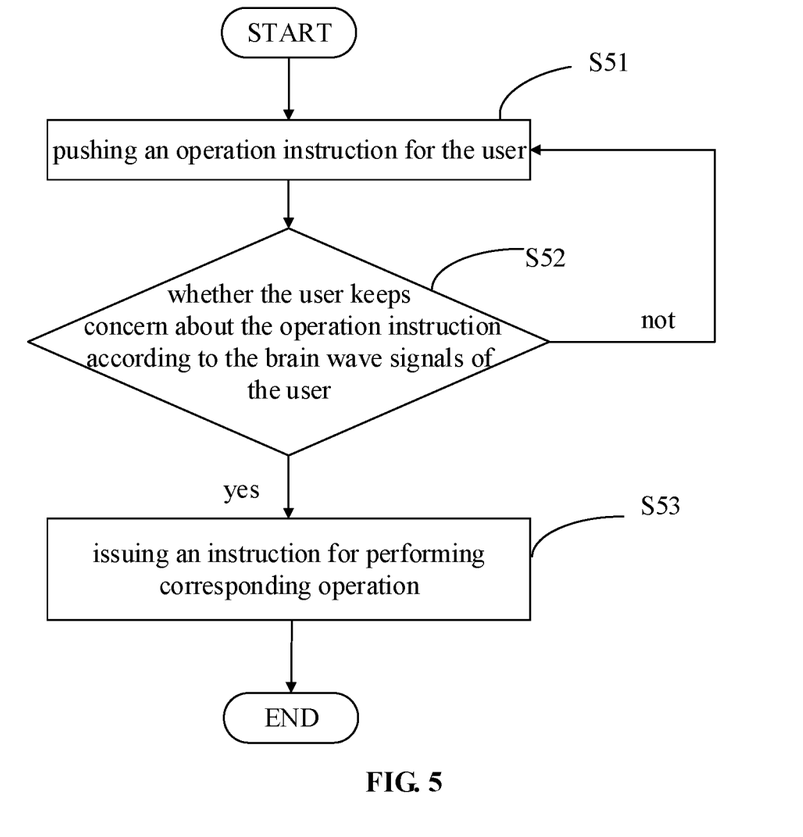
FIG. 5 is a flow chart of a vehicle control method according to still another embodiment of the present disclosure.

As another embodiment of the present disclosure, as shown in FIG. 5, the vehicle control method may further include: step S51 of pushing an operation instruction for the user; step S52 of determining whether the user keeps concern about the operation instruction according to the brain wave signals of the user; when determining that the user keeps concern about the operation instruction, performing step S53; otherwise, performing the step S51; step S53 of issuing an instruction for performing corresponding operation.

Specifically, after pushing the operation instruction for the user, it is determined whether the proportion of α waves in the brain wave signals of the user exceeds the α wave threshold according to the brain wave signals of the user; when determining that the proportion of α waves in the brain wave signals of the user exceeds the α wave threshold, an instruction for performing corresponding operation is issued. Optionally, the operation instruction is pushed for the user according to the user's behavior habits. The operation instruction may include a vehicle turning instruction, a speed instruction, a call connection instruction, a backlight brightness adjustment instruction, a music play instruction, and so on.

Thus, when the user needs to manipulate an instruction, the user only needs to keep a high degree of concern about the pushed operation instruction to enable the proportion of α waves in the brain wave signals of the user to exceed the α wave threshold, then an instruction for performing corresponding operation is issued so as to control corresponding components to perform corresponding operation. Therefore, under help of the above vehicle control method, the user's sight does not need to leave front road all the time, and the user only needs to control his brain waves, thereby greatly improving security.

In some embodiments of the present disclosure, the vehicle control method further includes: pushing an operation instruction for the user; and calculating a time period during which the user keeps concern about the operation instruction according to the brain wave signals of the user; when the time period during which the user keeps concern about the operation instruction exceeds a concern time threshold, issuing an instruction for performing corresponding operation.

Specifically, it may be determined whether the proportion of α waves in the brain wave signals of the user exceeds the α wave threshold according to the brain wave signals of the user; when determining that the proportion of α waves in the brain wave signals of the user exceeds the α wave threshold, starting timing; when the time period during which the user keeps concern about the operation instruction exceeds the concern time threshold, issuing an instruction for performing corresponding operation.

Since the above method is similar to the device embodiment, description of the above method is simple, related portions may refer to description of the device embodiment and will not be elaborated herein.

Figure 6:
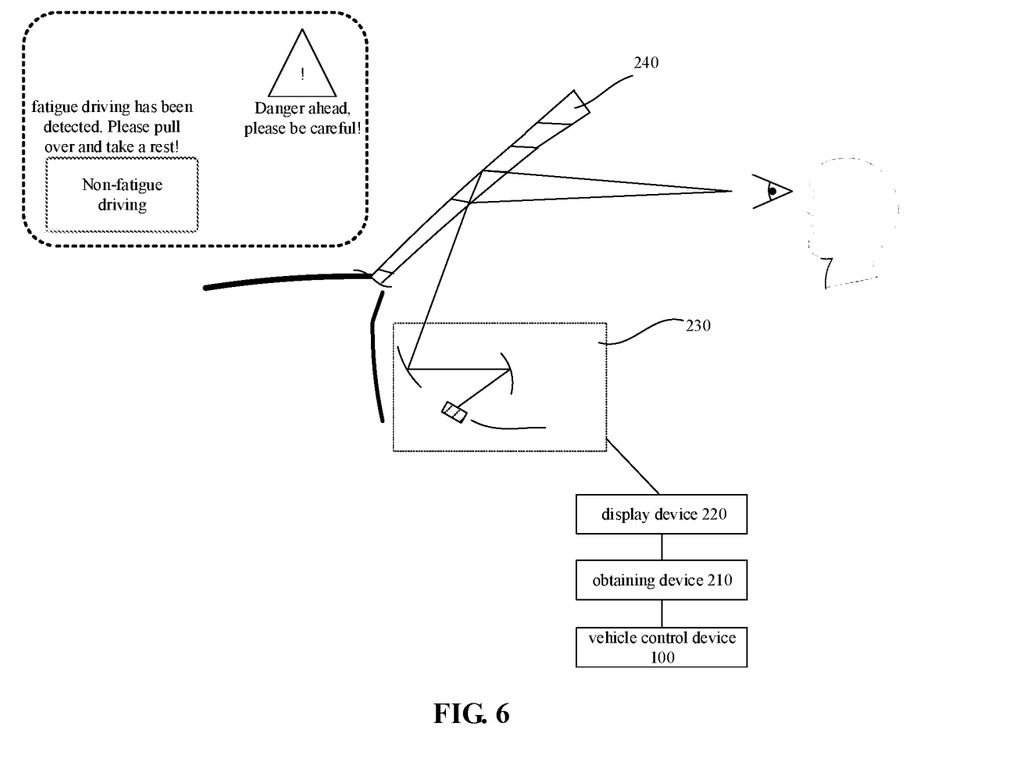
FIG. 6 is a schematic block diagram of a head-up display apparatus according to an embodiment of the present disclosure.

One embodiment of the present disclosure further provides a head-up display apparatus. As shown in FIG. 6, the head-up display apparatus includes an obtaining device 210, a display device 220, a projection device 230, a display medium 240 and the above vehicle control device 100 of any one of above embodiments. An image displayed on the display device 220 is projected onto the display medium 240 through the projection device 230. The obtaining device 210 is used to obtain position information of a gaze point of the user's eyes on the display medium 240 or the display device 220. The control circuit 120 of the vehicle control device 100 is used to issues an instruction for performing an operation corresponding to the position information according to the position information of the gaze point. Specifically, the projection device 230 includes a projection mirror and other optical components. Signal light source generated by light emitted from the display device 220, and is projected onto the display medium 240 through the projection mirror and a series of optical components, thereby displaying an image on the display medium 240. Optionally, the display medium 240 is a front windshield for facilitating the user to view contents displayed by the display device 220. The control circuit 120 is used to determine whether the user is in an unsafe driving state according to the brain wave signals; when determining that the user is in the unsafe driving state, the display device 220 displays a text reminder (which is accordingly projected onto the display medium 240), to remind the user to be in the unsafe driving state at this time.

In order to improve the safety of driving, contents projected onto the display medium 240 are small and concise. Arrow marking direction, overspeed condition, front obstacle, call reminder, music play and the like may be projected into the display medium 240.

As another embodiment of the present disclosure, the push circuit 130 of the vehicle control device 100 pushes an operation instruction for the user, and the operation instruction is displayed on the display device 220 (the operation instruction is also projected onto the display medium 240). The control circuit 120 determines whether the user keeps concern about the operation instruction currently displayed on the display device 220 or the display medium 240 according to the brain wave signals of the user; when determining that the user keeps concern about the operation instruction currently displayed on the display device 220 or the display medium 240, the push circuit 130 issues an instruction for performing corresponding operation. Therefore, under help of the above head-up display apparatus, the corresponding operation can be performed when the user's sight does not need to leave front road all the time, thereby greatly improving security.

As another embodiment of the present disclosure, the obtaining device 2210 includes an infrared emitter and a position calculation circuit. The infrared emitter is used to emit infrared light towards eyes of the user, thereby forming light reflection points in the two pupils of eyes of the user. The position calculation circuit is used to determine the position information of a gaze point of the user's eyes on the display medium 240 or the display device 220 according to the reflection points. It should be noted, the display device 220 and the display medium 240 can respond to the reflection points. Thus, based the eyes of the user, the head-up display apparatus can realize the operation corresponding to the position of the gaze point, thereby improving safety of driving. In one embodiment, the position calculation circuit may be implemented as a processor.

Figure 7:
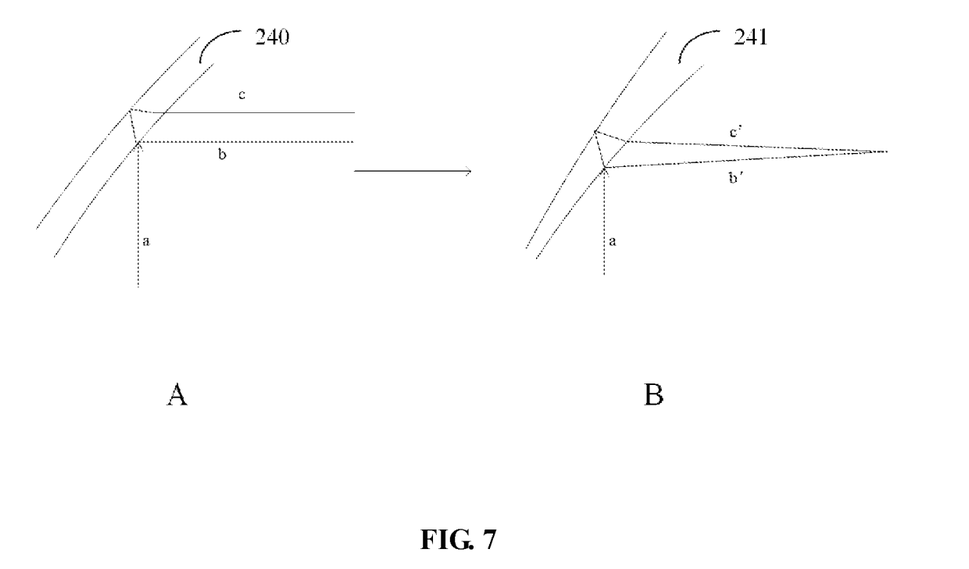
FIG. 7 is a schematic diagram showing light paths before and after the presence of a transflective film.

As another embodiment of the present disclosure, as shown in FIG. 7, the display medium 240 is a windshield which may be made of transparent glass or transparent plastic. A wedge-shaped transflective film 241 is disposed at an inner surface of the display medium 240. The transflective film 241 has a thickness that is gradually increased from a bottom of the vehicle to a top of the vehicle. A lower part of the transflective film 241 has a thickness is less than a thickness of an upper part of the transflective film 241. The transflective film 241 has an angle in a range of from 0.02-2.2 degrees. The angle of the transflective film 241 refers to an angle defined between an inner surface of the transflective film 241 and an outer surface of the transflective film 241. FIG. 7A is a schematic diagram showing light paths without a transflective film, and FIG. 7B is a schematic diagram showing light paths with a transflective film. Taking the windshield which is made of glass as an example, a represents an incident light, b represent a light reflected by an inner surface of the glass, c represents a light reflected by an inside surface of the glass, b' represents light reflected by an inner surface of the transflective film, and c' represents a light reflected by an outer surface of the transflective film. It should be noted, "inner" refers to one side facing towards an inside of the vehicle, and "outer" refers to way from the inside of the vehicle. As can be seen from FIG. 7, according to prism refraction and optical path difference, the transflective film 241 enables the light reflected by the inner surface of the transflective film and the light reflected by the outer surface of the transflective film to have overlap areas, then virtual and real images are integrated, thereby solving problems such as reflective halo on a windshield and picture ghosting.

Generally speaking, the display brightness of the head-up display apparatus is to be 15-300% of the brightness of ambient light, preferably 50%, too bright or too dark may cause the driver to not take into account road conditions and displayed images. As one embodiment of the present disclosure, the head-up display apparatus further includes an ambient light detection device. The ambient light detection device is used to detect brightness of the ambient light. The control circuit 120 of the vehicle control device is used to, when the brightness of the ambient light is less than a first brightness threshold and the gaze point is not at the display medium and the display device, send an instruction for reducing backlight brightness to the display device. The control circuit 120 is further used to, when the brightness of the ambient light is greater than a second brightness threshold and the gaze point is at the display medium and the display device, send an instruction for increasing backlight brightness to the display device. The second brightness threshold is greater than the first brightness threshold. In one embodiment, the ambient light detection device may include an ambient light sensor.

The head-up display apparatus provided in one embodiment of the present disclosure can adjust its brightness according to the user's intuitive perception, thereby allowing each user to really see the head-up display image without affecting the observation of road conditions. In order to improve the accuracy of judgment, the obtaining device 210 is also used to determine the gaze point of the eyes of the user. When the ambient light is dark (i.e., the brightness of the ambient light is less than the first brightness threshold) and the user feels that the head-up display image affects observation of road conditions, the obtaining device 210 cannot obtain the gaze point at the display medium and the display device and then the obtaining device 210 sends an instruction for reducing backlight brightness to the display device, so as to make head-up display image less distracting. When the ambient light is bright (i.e., the brightness of the ambient light is greater than the second brightness threshold) and the user normally looks straight ahead, the obtaining device 210 obtains the gaze point at the display medium and the display device and then the control circuit 120 sends an instruction for increasing backlight brightness to the display device.

Therefore, the head-up display apparatus provided in one embodiment of the present disclosure can adjust backlight brightness of the display device according to the user's intuitive perception of brightness differences based on the user's individual vision, thereby making the user more comfortable when viewing projected images on the display medium.

As another embodiment of the present disclosure, the control circuit 120 of the vehicle control device is used to, when the brightness of the ambient light is less than the first brightness threshold and the gaze point is not at the display medium and the display device, it is to determine whether the user keeps concern about the instruction for reducing backlight brightness; when determining that the user keeps concern about the instruction for reducing backlight brightness, the instruction for reducing backlight brightness is sent to the display device. When the ambient light is bright and the gaze point is at the display medium and the display device, it is to determine whether the user keeps concern about the instruction for increasing backlight brightness; when determining that the user keeps concern about the instruction for increasing backlight brightness, the instruction for increasing backlight brightness is sent to the display device.

Specifically, the control circuit 120 determines whether the proportion of α waves in the brain wave signals of the user exceeds the α wave threshold according to the brain wave signals of the user. Thus, when the user needs to control the backlight brightness, the user needs to keep a high degree of concern about the instruction for adjusting the backlight brightness to enable the proportion of α waves in the brain wave signals of the user to exceed the α wave threshold, then the control circuit 120 can send the instruction for adjusting backlight brightness, thereby controlling the backlight brightness. This can greatly improve control accuracy and efficiency. As another embodiment of the present disclosure, the control circuit 120 further calculates a time period during which the user keeps concern about the instruction for adjusting backlight brightness according to the brain wave signals of the user; when the time period during which the user keeps concern about the instruction for adjusting backlight brightness exceeds a concern time threshold, it is determined that the user keeps concern about the instruction for adjusting backlight brightness.

The head-up display apparatus provided in one embodiment of the present disclosure can adjust its brightness according to the user's intuitive perception and feedback of the brain waves, thereby allowing each user to really see the head-up display image without affecting the observation of road conditions.

As another embodiment of the present disclosure, the projection device 230 may be mounted in an instrument panel. The display device 220 includes a liquid crystal display module and a backlight module. Due to high requirements for image brightness (which is usually tens of thousands of nit to be visible to the human eyes), the backlight module adopts ultra-bright small micro-LEDs. However, the penetration rate of command liquid crystal display screens is less than 8%, a lot of heat may be generated by a color filter generate when the color filter absorbs some color lights, and the screen may be easily burn by the heat. Thus, the liquid crystal display module provided in one embodiment of the present disclosure adopts full glass structure without the typical color filter and polymer films, and structures such as a color filtering structure, a polarization structure and a light guiding structure are integrated at a glass substrate, and then the penetration rate may reach over 30%, thereby preventing the color filter from generating a lot of heat. Optionally, optical structures for deflecting light may be added to a front surface or a backlight side of the liquid crystal display module, thereby adjusting an angle along which light emitted out, without reducing the brightness. The optical structures may be a lenticular grating, may be independent or be multiplexed with other structural layers, thereby avoiding reflection of light leaked from image information in the windscreen.

As described above, the vehicle control device, the vehicle control method and the head-up display apparatus can determine whether the user is in the unsafe driving state according to the brain wave signals of the user, and make corresponding reminders or deceleration controls when the user is in the unsafe driving state. In this way, the safety of user driving and the recognition accuracy are improved. Further, in the head-up display apparatus provided in one embodiment of the present disclosure, the presence of the wedge-shaped transflective film enables the light reflected by the inner surface of the transflective film and the light reflected by the outer surface of the transflective film to have overlap areas, then virtual and real images are integrated, thereby solving problems such as reflective halo on a windshield and picture ghosting.

Through description of the above embodiments, technical personnel of the field can clearly understand that the present invention can be realized depending on software and necessary general hardware platform, and it also can be realized through hardware, while the former is better in many cases. Based on this understanding, the technical solution of the present invention or the part making contributions to available technology can be essentially reflected by means of software product. This computer software product is stored in a storage medium, including several instructions to enable a terminal unit (such as handset, personal computer, sever, or network equipment, etc.) to implement the methods described in all embodiments of the present invention.

Only the preferred embodiments of the present invention are mentioned above. It shall be pointed out that technical personnel of the technical field can make any improvement and modification, which also shall be protected by the present invention.

Technician of this field can understand that module in device of embodiment can be distributed thereof according to the description and also can be distributed in one or more devices that is different from this embodiment. Modules of said embodiments can be integrated or deployed in separation, or combined as a module and even dismantled into several sub-modules.

The number of the aforementioned embodiments of the present invention is only used for description rather than for representing advantages or disadvantages.

The above are merely the optional embodiments of the present disclosure and shall not be used to limit the scope of the present disclosure. It should be noted that, a person skilled in the art may make improvements and modifications without departing from the principle of the present disclosure, and these improvements and modifications shall also fall within the scope of the present disclosure.

What is claimed is:

1. A vehicle control device comprising:
   a brain wave extractor configured to extract brain wave signals of a user; and
   a vehicle safety control circuit configured to determine whether the user is in an unsafe driving state according to the brain wave signals, and perform at least one of operations including issuing a warning reminder and controlling vehicle deceleration when determining that the user is in the unsafe driving state;
   wherein the vehicle safety control circuit is further configured to, according to the brain wave signals, determine whether a proportion of $\theta$ waves in the brain wave signals exceeds a $\theta$ wave threshold, whether a proportion of $\beta$ waves in the brain wave signals exceeds a $\beta$ wave threshold, or whether a proportion of $\gamma$ waves in the brain wave signals exceeds a $\gamma$ wave threshold;
   when determining that the proportion of $\theta$ waves in the brain wave signals exceeds the $\theta$ wave threshold, the proportion of $\beta$ waves in the brain wave signals exceeds the $\beta$ wave threshold, or the proportion of $\gamma$ waves in the brain wave signals exceeds the $\gamma$ wave threshold, the vehicle safety control circuit performs at least one of operations including issuing the warning reminder and controlling vehicle deceleration;
   wherein the vehicle control device further comprises a push circuit configured to push an operation instruction for the user;
   wherein the vehicle safety control circuit is further configured to determine whether the user is concerned about the operation instruction according to the brain wave signals of the user; when determining that the user is concerned about the operation instruction, the vehicle safety control circuit issues an instruction for performing corresponding operation;
   wherein the vehicle safety control circuit is further configured to, after the push circuit pushes the operation instruction for the user, determine whether a proportion of $\alpha$ waves in the brain wave signals of the user exceeds a $\alpha$ wave threshold according to the brain wave signals of the user; and determine that the user is concerned about the operation instruction, when the proportion of $\alpha$ waves in the brain wave signals of the user exceeds the $\alpha$ wave threshold.

2. The vehicle control device of claim 1, wherein the $\theta$ wave has a frequency of 4 Hz-7 Hz as well as an amplitude of 5 $\mu$V-20 $\mu$V; the $\beta$ wave has a frequency of 14 Hz-30 Hz as well as an amplitude of 100 $\mu$V-150 $\mu$V; and the $\gamma$ wave has a frequency of 30 Hz-80 Hz.

3. The vehicle control device of claim 1, wherein the vehicle safety control circuit is further configured to calculate a time period during which the user is in the unsafe driving state; when the time period during which the user is in the unsafe driving state exceeds an unsafe time threshold, the vehicle safety control circuit controls a vehicle to stop.

4. The vehicle control device of claim 1, wherein the operation instruction includes at least one of a vehicle turning instruction, a speed instruction, a call connection instruction, a backlight brightness adjustment instruction or a music play instruction.

5. The vehicle control device of claim 4, wherein the $\theta$ wave has a frequency of 4 Hz-7 Hz as well as an amplitude of 5 $\mu$V-20 $\mu$V.

6. The vehicle control device of claim 1, wherein the brain wave extractor includes an electrode cap.

* * * * *